US00PP29767P3

(12) United States Plant Patent
Lehmann

(10) Patent No.: US PP29,767 P3
(45) Date of Patent: Oct. 23, 2018

(54) AVOCADO ROOTSTOCK NAMED 'KB1'

(50) Latin Name: ***Persea americana* Mill.**
Varietal Denomination: KB1

(71) Applicant: Klaus Bederski Lehmann, Lima (PE)

(72) Inventor: Klaus Bederski Lehmann, Lima (PE)

( * ) Notice: Subject to any disclaimer, the term of this patent is extended or adjusted under 35 U.S.C. 154(b) by 0 days.

(21) Appl. No.: 15/530,161

(22) Filed: Dec. 6, 2016

(65) Prior Publication Data

US 2018/0160584 P1 Jun. 7, 2018

(51) Int. Cl.
*A01H 5/08* (2018.01)

(52) U.S. Cl.
USPC ..... Plt./200
CPC ..... *A01H 5/08* (2013.01)

(58) Field of Classification Search
USPC ..... Plt./200
See application file for complete search history.

*Primary Examiner* — Susan McCormick Ewoldt
(74) *Attorney, Agent, or Firm* — Kelly & Kelley, LLP

(57) ABSTRACT

A new avocado variety, 'KB1', was discovered in Chincha, Peru. The 'KB1' variety when used as a rootstock is notable for its prolific and vigorous feeder root growth ability that results in rapid canopy volume and early productivity of the 'Hass' avocado scion cultivar, and induces larger fruit sizes of the 'Hass' cultivar and is an alternative for locations where ecologic conditions tend to produce small fruit.

9 Drawing Sheets

Latin name of the genus and species: *Persea americana* Mill.

Varietal denomination: 'KB1'.

BACKGROUND OF THE INVENTION

Historically, avocado scion varieties were propagated by grafting them over seedling rootstocks of three origins: Mexican, Guatemalan and West Indian. Each growing area used the alternative best suited to its proper ecologic conditions. California chose seedling rootstocks of Mexican origin, typically 'Topa Topa' (unpatented). Florida chose seedling rootstocks of West Indian origin, typically 'Waldin' (unpatented). Seedling rootstocks proved to be variable in their morphological and productive characteristics. The avocado industry demanded more uniformity in growth and productivity of orchard trees than trees on seedling rootstocks were able to provide.

The search for an answer led to the development of clonal rootstocks where all trees in an orchard were genetically identical to each other. Eventually, 'Duke 7' (unpatented) became the leading clonal avocado rootstock for California. This clonal rootstock, and more recently also the 'Merensky 2' (U.S. Plant Pat. No. 15,309) clonal rootstock, have been introduced for cultivation worldwide. Clonal avocado rootstocks, like seedling avocado rootstocks, are not necessarily best suited to the particular soil-water-climate conditions of all avocado growing regions world-wide.

Currently, the main avocado variety grown in the word is 'Hass' (U.S. Plant Pat. No. 139, the contents of which are incorporated herein by reference). The main markets have year-round supply of 'Hass' avocados and end consumers are very used to buying 'Hass'. Many other avocado varieties have been created and patented in the last twenty years, but none of them has been able to obtain important interest from growers. The main reason for the lack of interest is that the market still prefers 'Hass'.

SUMMARY OF THE INVENTION

'KB1' is a new and distinct variety of avocado tree *Persea americana* Mill. 'KB1' is a clonal avocado rootstock that has rapid uniform growth and early productivity.

In approximately 1998, during a weekend family tour into a remote rural area located in Andean Highlands Mr. Bederski Lehmann saw a large well-foliated avocado tree growing in an orchard where most of the surrounding trees were small and showed poor canopy growth. The area, Santa Eulalia Valley, east of the city of Lima, Peru is known for the endemic presence of the avocado root rot fungus *Phytophthora cinnamomi* Rands.

A handmade stone and mud wall about four feet high with cacti growing on top of the wall separated the unpaved road from the orchard where this tree was growing. Corn had been planted in the middle rows, as is often done as an added source of income for peasant family owned properties in that valley. The owner was cultivating this field with a mule-driven plow.

Mr. Bederski Lehmann asked him if he could see this tree. Mr. Bederski Lehmann was allowed to enter the property and evaluate this outstanding tree which he named "Tree X", which had a healthy, extensive root system contrasting with the limited and necrotic roots of most surrounding trees. Mr. Bederski Lehmann noticed that the "Tree X" had been grafted to a 'Fuerte' cultivar (unpatented) and that management neglect had allowed water sprouts to grow from the rootstock. The oldest of those sprouts had grown to become a mature lateral trunk that had found its way through the 'Fuerte' canopy and had developed a canopy of its own which had mature fruit the day Mr. Bederski Lehmann was there. Mr. Bederski Lehmann observed that the fruits had typical Mexican characteristics and that the leaves had anise odor which was also typically Mexican. However, he also observed that the tips and leaves of newly growing shoots had a reddish color that suggested it could also contain genes of the Guatemalan race of avocados. Mr. Bederski Lehmann was intrigued by the fact that he was observing Mexican and Guatemalan traits occurring simultaneously in the sprouts arising from the rootstock of this "Tree X". Mr. Bederski Lehmann arranged with the owner to obtain fruits and budsticks from this water sprout of "Tree X".

Mr. Bederski Lehmann took the seeds and budsticks from the sprout of "Tree X" to his own property, which includes a fruit tree nursery. Mr. Bederski Lehmann planted the seeds from the fruit of "Tree X" in nursery poly bags. Mr. Bederski Lehmann also topworked the budsticks on a group of young 'Topa Topa' (unpatented) trees in a cultivated area of his property.

The seedlings that grew from these seeds did not show the genetic uniformity that is required by nurseries and by growers of the avocado industry. Their extreme variability in vigor as well as in the color and leaf characteristics suggested that this rootstock source had an unexpected genetic complexity. Mr. Bederski Lehmann decided not to use "Tree X" as a source of seeds for sexual avocado propagation.

The budsticks of "Tree X" that had been topworked onto the group of young 'Topa Topa' trees grew uniform and fast and started flowering approximately a year later. By coincidence, a group of Peruvian West Indian avocado trees ('Villa Campa', 'Brillosa' and 'Huevo de Toro') (all unpatented) was growing next to the topworked "Tree X" trees and had the same flowering period as the "Tree X" trees. Mr. Bederski Lehmann had all of the trees covered with an anti-insect screen and placed a beehive inside. The screen was taken away at the end of the blooming period and approximately one year later fruits were harvested from the "Tree X" topworked trees, categorized according to the "Tree X" topworked tree they were taken from and allowed to grow. Mature budsticks were obtained from each of these numbered seedlings and topworked over the "Tree X" topworked 'Topa Topa' trees from which they had originated. Approximately two years after this topworking, Mr. Bederski Lehmann observed that the bark from only one of the numbered seedlings and also the bark of the topworked portion of the same numbered topworked tree started showing long, horizontal, thick, dark brown lenticels, implying that it could have been the chance hybrid with the Peruvian West Indian avocado trees which have characteristics and traits of being better adapted than other rootstocks to the arid, saline alkaline soils of the Peruvian coastal areas. This one source became the Foundation Tree of the new avocado variety named 'KB1'.

The Foundation Tree of the 'KB1' clonal avocado rootstock is located on the property of the inventor, Mr. Bederski Lehmann in Chincha, Peru. The Foundation Tree has provided the material to establish the techniques for clonal propagation under local conditions and for initial trial plantings of 'Hass' avocados on 'KB1' clonal that had been established exclusively in Mr. Bederski Lehmann's property.

'Hass' avocado on 'KB1' clonal rootstock was planted for limited trial at the inventor's property in 2010 and in 2013. 'Hass' on 'KB1' clonal rootstock at this location soon proved to be a superior alternative exhibiting uniform rapid growth and early productivity when compared to conventional 'Hass' on seedling rootstocks. The 'KB1' variety has remained stable in all of its initial characteristics and has been developed to be used only as a clonal rootstock for avocados. It develops an extensive and vigorous feeder root system favoring rapid canopy development and early productivity of the 'Hass' variety. 'KB1' has anise scented leaves, typical of the Mexican race of avocado, reddish colored young leaves and growing tips that characterize the avocados of the Guatemalan race, and large visible horizontal lenticels that can be associated with the West Indian race of avocados.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying photographs show specimens of the tree and plant parts of the new 'KB1' variety.

DETAILED BOTANICAL DESCRIPTION OF THE VARIETY

The following detailed botanical description is based on observations of a 'KB1' rootstock variety which was taken from an approximately sixteen-year-old mature tree, planted in 2000 in Chincha, Peru, and evaluations conducted in 2016 for 'Hass' on 'KB1' clonal rootstock planted between 2010 and 2014 in Chincha, Peru.

In those instances where precise color assessment could be made, references are to The Royal Horticultural Society (R.H.S.) Colour Chart Sixth Edition (2015). In other instances, generally, color terms are used in accordance with an ordinary dictionary significance. Other descriptions are taken from the generally recognized description chart found in the *Graphic Handbook for the Description of Avocado Varieties* published by SAGARPA in January, 2010 (ISBN: 978-607-12-0106-5) ("Graphic Handbook").

Figure 1:
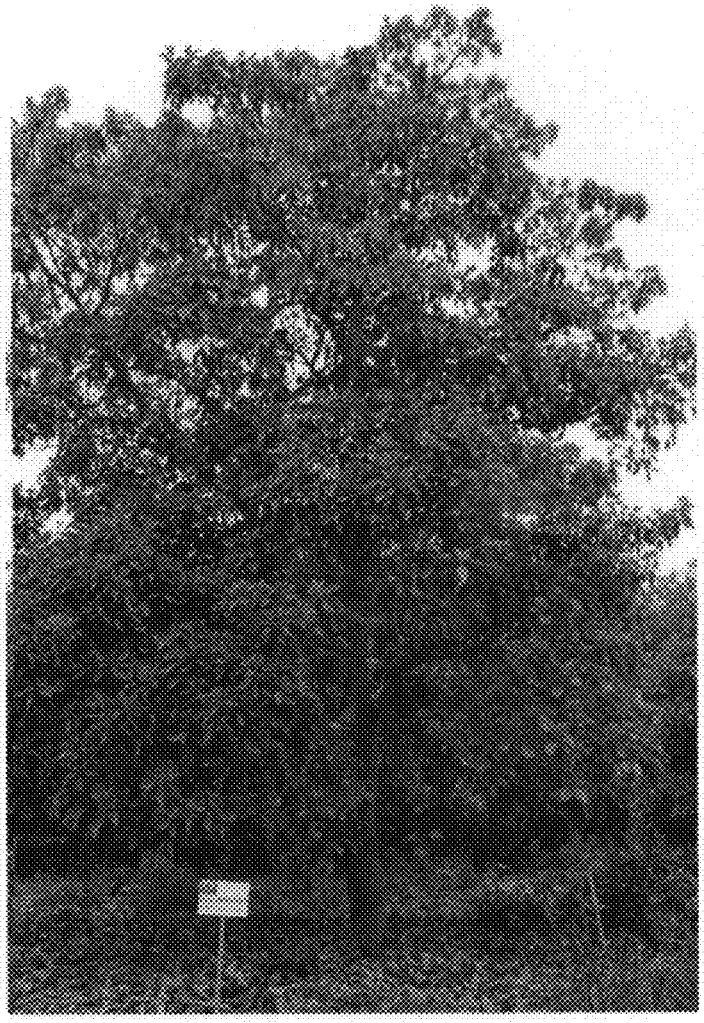
FIG. 1 is a photograph of the 'KB1' foundation tree growing in Chincha, Peru.

With reference to FIG. 1, the 'KB1' foundation tree is shown which was planted in 2000 in Chincha, Peru. The tree is now approximately eight meters tall and six meters in diameter. An aspect of 'KB1' is that it has rapid uniform growth. The 'KB1' has a generally upright tree shape. The color of a one-year-old branch is strong yellow green (RHS 144B). Young shoots have a soft, juicy texture. The color of expanding apical leaves of young shoots is moderate yellowish brown (RHS N199C).

Figure 2:
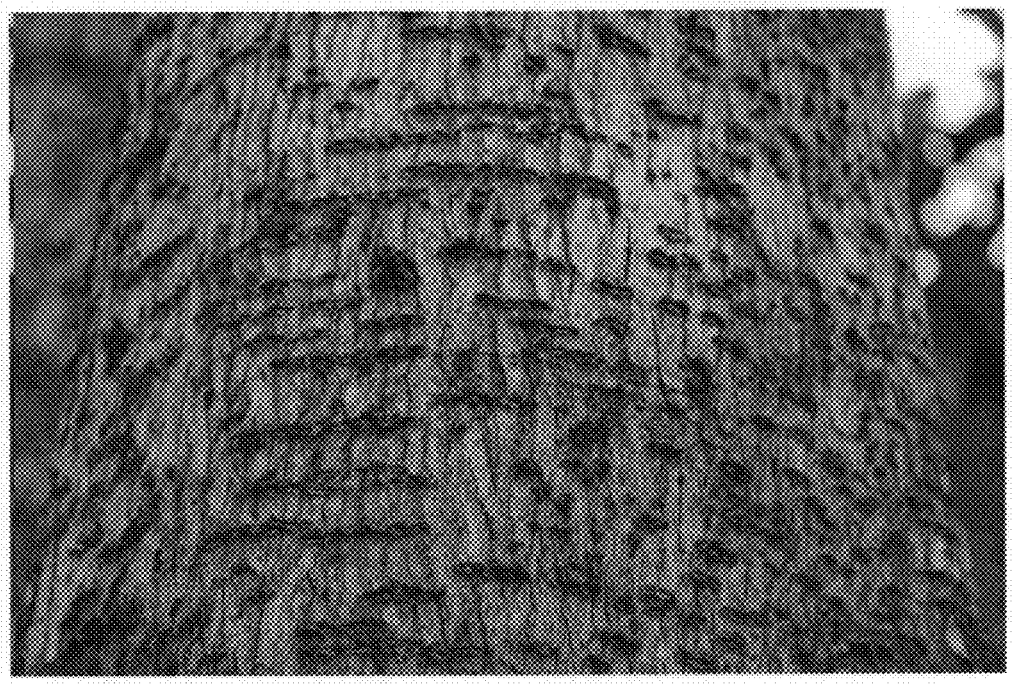
FIG. 2 is a photograph depicting lenticels of the 'KB1' variety.

As illustrated in FIG. 2, the lenticels found on the 'KB1' tree are big, long and horizontal. The color of the lenticels (one-year-old bark) are moderate brown (RHS 200C). The bark texture of a one-year-old branch is smooth. One-year-old bark has a moderate orange yellow color (RHS 165C), while the oldest bark growth has a dark grayish yellow color (RHS 199D).

Figure 3:
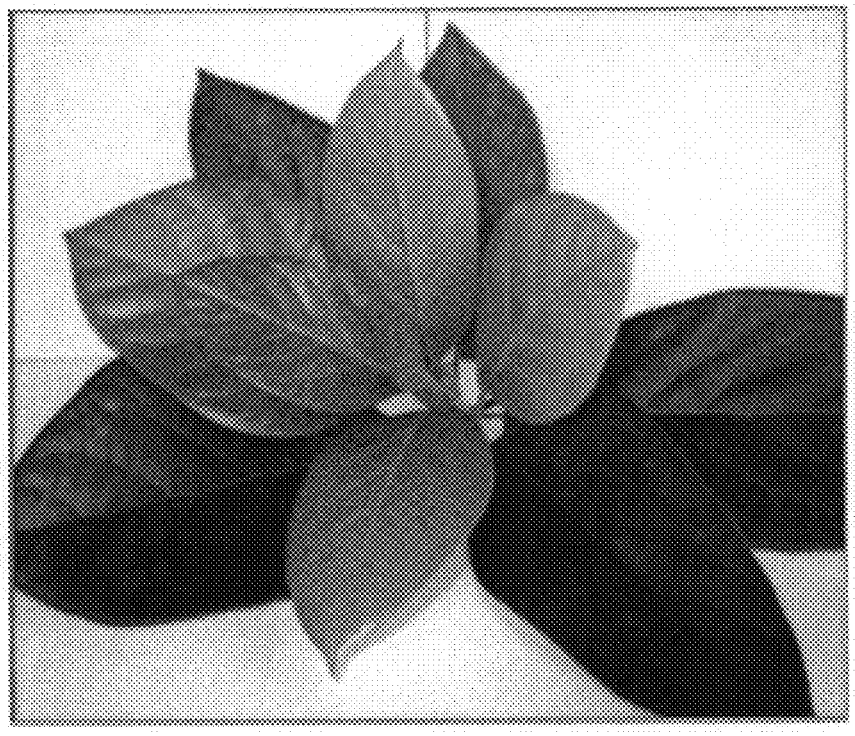
FIG. 3 is a photograph depicting flush foliage of the 'KB1' variety.

FIG. 3 illustrates typical flush foliage of 'KB1'. The young shoot color is moderate yellowish brown (RHS N199C). The leaf blade anise aroma is strong, indicating Mexican origin. The Graphic Handbook uses the presence or absence of anise smell in the leaf blade as an indication of the tree origin; West Indian having no smell, whereas Mexican has anise smell.

The leaf arrangement is alternate relative to shoot (Graphic Handbook). Mature leaves have a weak undulation margin. The leaf venation pattern of a mature, fully expanded leaf is camptodromous, pinnate venation, as illustrated. An upper surface vein has a brilliant greenish yellow color (RHS 151D). The veins of a mature, fully-expanded leaf are level (Graphic Handbook). A mature, fully expanded, leaf typically has an intermediate number of secondary veins between 14.5 and 17.5 secondary veins on the leaf blade.

The density of pubescence on the lower surface of a mature leaf is medium. Medium density of pubescence on the lower surface of a mature leaf is shown in the Graphic Handbook under element 17. Texture of upper surface of mature leaves is smooth.

Twisting along the whole length of the leaf blade of a mature leaf is absent. The shape of the apex of the leaf blade is acuminate. The leaf base shape of a mature, fully expanded leaf is equilateral. The leaf blade length is medium (16.1 cm-18.4 cm) (Graphic Handbook). The leaf blade width of a mature, fully expanded leaf is also medium (6.6 cm-7.6 cm) (Graphic Handbook).

The color of the upper surface of a mature fully expanded leaf is greyish olive green (RHS NN 137B). The color of the lower surface of a mature, fully expanded leaf is pale green (RHS N 138C). The color of tender, fully grown leaves is moderate olive green (RHS 146A).

The length of a mature, fully expanded leaf petiole is medium (between 3.9 cm and 4.62 cm) (Graphic Handbook). The diameter of a mature, fully expanded leaf petiole is approximately 2.5 mm. The color of a mature, fully expanded leaf petiole is moderate yellow green (RHS 146C).

Figure 4:
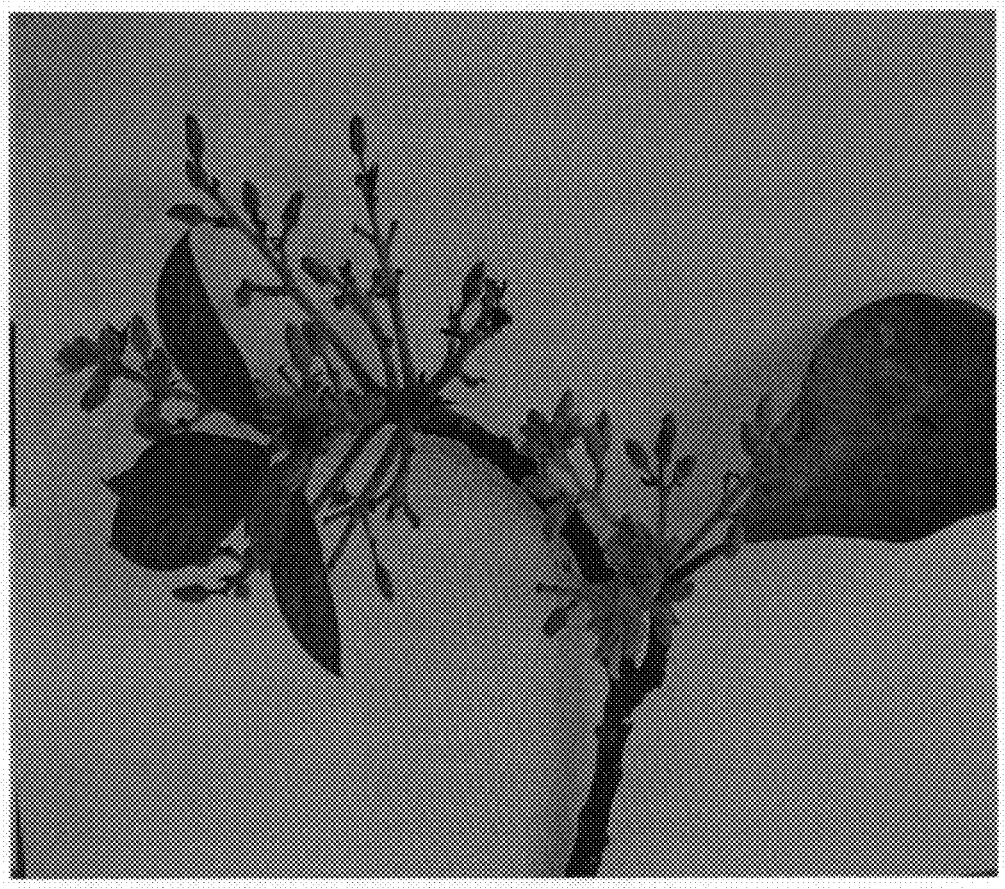
FIG. 4 is a photograph depicting inflorescence of the 'KB1' variety.

With reference now to FIG. 4, typical inflorescence of the 'KB1' variety is shown. The cutting illustrated measures approximately 4.09 cm-6.53 cm. The 'KB1' variety has a B flowering type. The flower fragrance of a fully opened flower is absent. The perianth (sepals and petals) of a newly, fully opened flower is borne in two whorls of three perianth lobes. The length of a fully developed flower bud is approximately nine millimeters, and the diameter is approximately five millimeters. There are nine stamen of a fully opened flower. The pistil of the fully opened flower has one each of a stigma, style and ovary. The ovary is superior. The color of a fully developed flower bud is brilliant yellow green (RHS 150C). The petal color of the fully opened flower, on both surfaces, is light yellow green (RHS 154C).

In its native Peru, the spring bloom period extends from early August through mid-October. 'KB1' rarely has off-season flowers. Fruit set is poor and only a very few fruits ripen.

Figure 5:
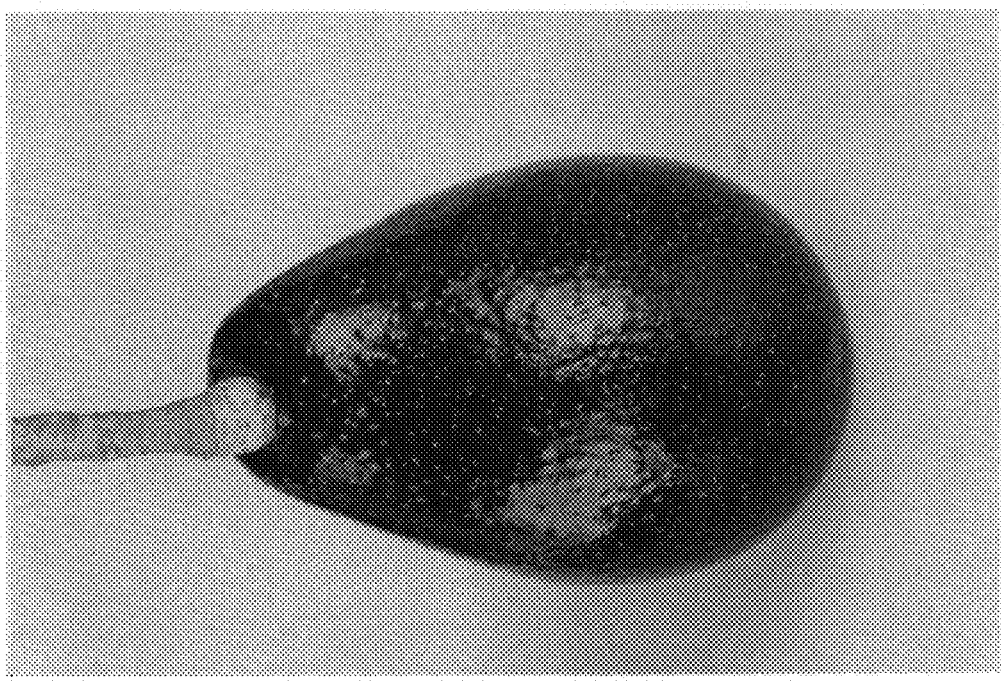
FIG. 5 is a photograph depicting an external view of the fruit of the 'KB1' variety.

With reference to FIG. 5, an exterior view of a typical fruit of the 'KB1' variety is shown. The diameter of the fruit measures 6.60 cm-8.33 cm on average so as to have a relatively small mature fruit diameter, such as an 'Edranol'. The length of the fruit on average measures 10.71 cm-13.23 cm, which is short, as in 'Edranol'. However, the mature fruit ratio length/diameter is medium, as in 'Topa Topa'. The average fruit weight, taken from an average of six mature fruit, is 159 grams.

The color of the fruit skin as it starts to change color is strong yellow green (RHS 143A). Phase 2 in color change of the fruit skin, the color is dark red (RHS 183B). The mature fruit skin color is dark red (RHS 187A). The fruit skin color of a fully ripe fruit is black (RHS 203B).

With continuing reference to FIG. 5, the length of the fully expanded pedicel is short, between 0.99 and 1.45 cm. The shape of the pedicel is conical and does not exhibit a "nailhead" at the junction. The thickness of the fully expanded pedicel compared to peduncle at junction is thicker, approximately 2 mm. The pedicel surface texture is wrinkled. The fully expanded peduncle is approximately 3.56 cm, with a diameter of approximately 3.2 mm. The color of the fully expanded peduncle is strong greenish-yellow (RHS 151A).

Figure 6:
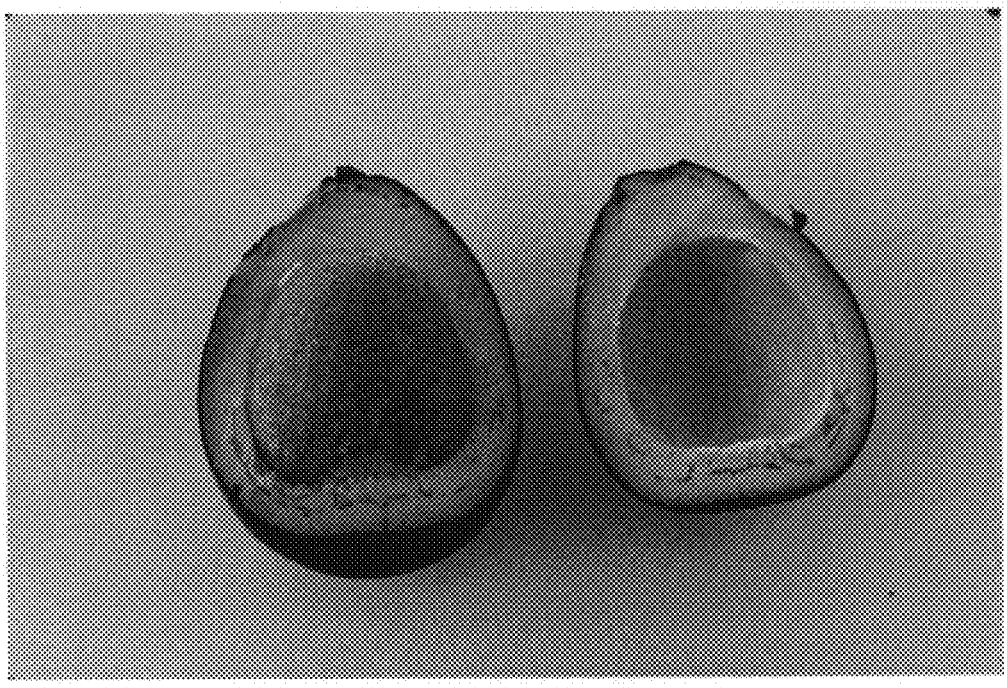
FIG. 6 is a photograph depicting an internal view of the fruit of the 'KB1' variety, with and without the seed.

FIG. 6 is a typical internal view of the 'KB1' variety fruit, illustrating with and without the seed. The shape of the seed in longitudinal section is generally ovate. The seed diameter at the widest equatorial point (taken from an average of four seeds) is 3.175 cm. The average seed length at polar ends, taken from the four seeds, is 4.445 cm. The average weight of the seed is 29.25 grams. The seed color is pale orange yellow (RHS 24D).

With continuing reference to FIG. 6, the color of the flesh of a fully ripe fruit is light yellow-green (RHS 145 B). The lenticel color of the fully ripe fruit is dark red (RHS 187B). As illustrated in FIGS. 5 and 6, the color of the ripe fruit is dark greyish purple (RHS 202A) or black (RHS 203B). The thickness of the skin of the ripe fruit is very thin.

An experimental block of 'Hass' avocado was planted in March 2014 at the inventor's property using four (4) rootstock sources: 'KB1' clonal, West Indian 'Waldin' seedlings, seedling selection and (hybrid) Mexican x Guatemalan 'Zutano' (unpatented) seedlings. Data taken in 2016 has shown that statistical differences do exist in canopy volume, early productivity, fruit weight (caliper) and cosmetic external quality. All of these measurements show 'KB1' clonal as the superior rootstock choice under the soil-water-climate conditions of this location. The following is the data of the 'KB1' avocado rootstock compared to other standard avocado rootstocks, as mentioned above, during the evaluation process in Peru and California.

TABLE 1

| Rootstock | Canopy Diameter (Meters) |
|---|---|
| 'Waldin' | 5.86 |
| Clonal 'KB1' | 7.68 |
| 'Zutano' | 5.96 |
| Seedling Selection | 5.55 |

Figure 7:
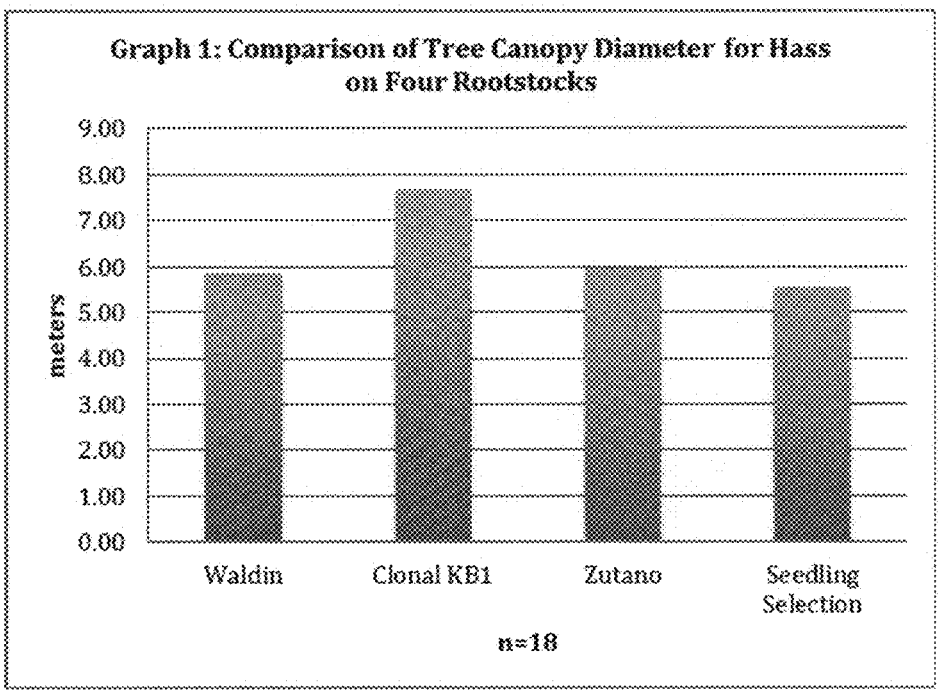
FIG. 7 is a graph depicting the comparison of tree canopy diameter for the 'KB1' variety as compared to other avocado varieties.

Table 1 above is the average diameter of the tree canopy for 'Hass' on the four different rootstocks, including the 'KB1' variety. FIG. 7 is a corresponding graph illustrating a comparison of the tree canopy diameter for 'Hass' for the four rootstocks of Table 1.

TABLE 2

| Rootstock | No. of Trees | Total Yield (KG) | Average Yield/Tree (KG) |
|---|---|---|---|
| Clonal 'KB1' | 92 | 728.64 | 7.92 |
| 'Waldin' | 80 | 551.43 | 6.89 |
| 'Zutano' | 84 | 522.82 | 6.22 |
| Seedling Selection | 73 | 58.64 | 0.80 |

Figure 8:
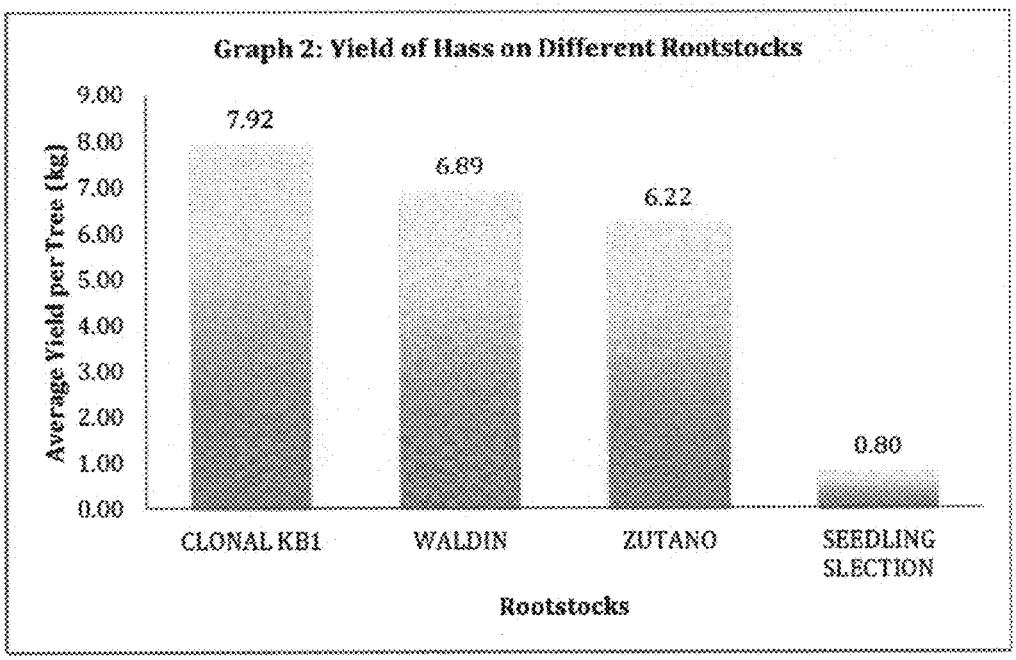
FIG. 8 is a graph depicting the yield of fruit for the 'KB1' variety as compared to other varieties.

Table 2 is a table illustrating the yield of 'Hass' on the different rootstocks. FIG. 8 is a graph depicting the yield of 'Hass' on the different rootstocks.

TABLE 3

| Rootstock | Fruit No. | Defective Fruit No. | Defective Fruit % |
|---|---|---|---|
| Clonal 'KB1' | 1483 | 16 | 1.08% |
| 'Zutano' | 955 | 87 | 9.11% |
| Seedling Selection | 218 | 28 | 12.84% |
| 'Waldin' | 1254 | 171 | 13.64% |

Figure 9:
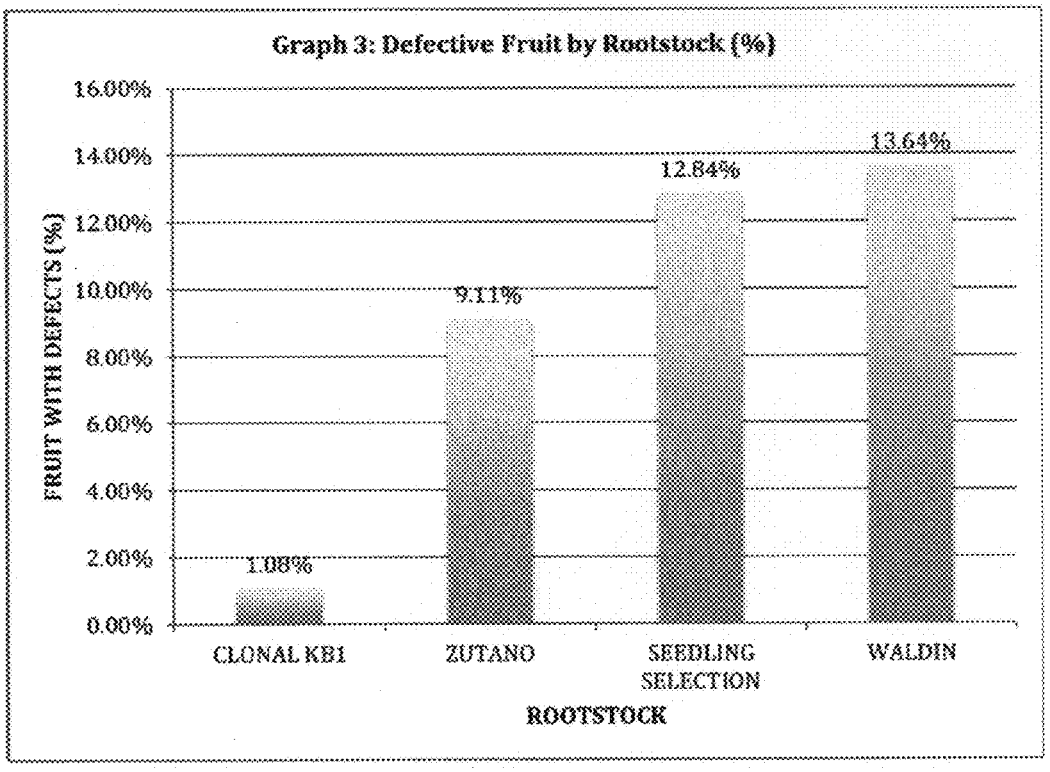
FIG. 9 is a graph depicting the percentage of defective fruit of the 'KB1' variety as compared to other avocado varieties.

Table 3 illustrates the incidents of defective fruit for the 'KB1' variety, as compared to the other three different rootstocks, and FIG. 9 is a graph depicting the percentage of defective fruit by rootstock.

As illustrated in Table 4 below, one hundred fruit per rootstock, including the 'KB1' variety as compared to the other varieties, from two-year-old trees were randomly selected and evaluated in order to classify the fruits by fruit counts (CODEX NORM).

TABLE 4

| | Count (g) | | | | |
|---|---|---|---|---|---|
| Rootstock | 8 (460-575) | 10 (365-460) | 12 (305-365) | 14 (265-305) | 16 (235-265) |
| Waldin | | 2% | 12% | 23% | 19% |
| Clonal KB1 | | 3% | 39% | | 38% |
| Zutano | 1% | 2% | | 24% | 33% |
| Seedling Selection | 1% | 2% | 13% | | 44% |

TABLE 4-continued

| | Count (g) | | | | |
|---|---|---|---|---|---|
| Rootstock | 18 (210-235) | 20 (190-210) | 22 (170-190) | 24 (155-170) | 26 (145-155) |
| Waldin | 32% | | 12% | | |
| Clonal KB1 | | 16% | | | 4% |
| Zutano | | 30% | | | |
| Seedling Selection | 32% | | | 8% | |

As shown in Table 5 below, the yield of the 'Hass' cultivar on the four rootstocks, including the 'KB1' variety, was measured in the two-year-old trees, and the yield extrapolated to one hectare.

TABLE 5

| Rootstock | Yield per tree (kg) | Distance (m) | Total number of trees per ha | Yield per ha (ton) |
|---|---|---|---|---|
| Clonal KB1 | 7.76 | 6 × 4 | 416 | 3.23 |
| Waldin | 6.89 | 6 × 4 | 416 | 2.87 |
| Zutano | 6.2 | 6 × 4 | 416 | 2.58 |
| Seedling Selection | 0.79 | 4 × 3 | 833 | 0.66 |

'KB1' is to be used commercially as a rootstock. As can be seen from the above, the new and distinct avocado variety 'KB1' when used as a rootstock confers to the tree a high yield and high vigor when topworked to 'Hass'. Moreover, the 'KB1' avocado rootstock cultivar variety is notable for its prolific and vigorous feeder root growth ability that results in rapid canopy volume and early productivity of the 'Hass' avocado scion cultivar. The 'KB1' variety induces larger fruit sizes of the 'Hass' cultivar and is an alternative for locations where ecologic conditions can produce small fruit, such as in well-drained alkaline soils in low rainfall conditions.

What is claimed is:

1. A new and distinct avocado rootstock, as herein illustrated and described.

* * * * *